(12) United States Patent
Wisler et al.

(10) Patent No.: US 6,459,262 B1
(45) Date of Patent: Oct. 1, 2002

(54) TOROIDAL RECEIVER FOR NMR MWD

(75) Inventors: Macmillan M. Wisler, Kingwood; Bryan L. Gonsoulin, Houston; Larry W. Thompson, Willis, all of TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/557,441

(22) Filed: Apr. 25, 2000

(51) Int. Cl.$^7$ ................................................. G01V 3/00
(52) U.S. Cl. ....................................................... 324/303
(58) Field of Search ................................ 324/303, 307, 324/309, 318, 320

(56) References Cited

U.S. PATENT DOCUMENTS

| | | | |
|---|---|---|---|
| 4,350,955 A | | 9/1982 | Jackson et al. .............. 324/303 |
| 4,629,986 A | | 12/1986 | Clow et al. .................. 324/303 |
| 4,714,881 A | * | 12/1987 | Givens ......................... 324/303 |
| 4,717,876 A | | 1/1988 | Masi et al. ................... 324/303 |
| 5,212,447 A | | 5/1993 | Paltiel .......................... 324/300 |
| 5,712,566 A | | 1/1998 | Taicher et al. ............... 324/303 |
| 5,814,988 A | * | 9/1998 | Itskovich et al. ............ 324/303 |
| 5,828,214 A | * | 10/1998 | Taicher et al. ............... 324/303 |
| 5,834,936 A | * | 11/1998 | Taicher et al. ............... 324/303 |
| 5,959,453 A | * | 9/1999 | Taicher et al. ............... 324/303 |
| 6,133,735 A | * | 10/2000 | Hurlimann et al. .......... 324/303 |
| 6,166,543 A | * | 12/2000 | Sezginer et al. ............. 324/303 |
| 6,179,066 B1 | * | 1/2001 | Nasr et al. ...................... 175/45 |
| 6,255,817 B1 | * | 7/2001 | Poitzsch et al. ............. 324/303 |

OTHER PUBLICATIONS

M.N. Miller et al., "Spin Echo Magnetic Resonance Logging: Porosity and Free Fluid Index Determination" 65th Annual Technical Conference and Exhibition, Sep. 23–26, 1990. SPE 20561, pp. 321–333.

* cited by examiner

Primary Examiner—Edward Lefkowitz
Assistant Examiner—Dixumara Vargas
(74) Attorney, Agent, or Firm—Madan, Mossman & Sriram, P.C.

(57) ABSTRACT

An NMR apparatus includes permanent magnets oppositely polarized in the axial direction and suitably arranged along the axis of the apparatus to produce a nearly radial static magnetic field in a toroidal examination region within the rock formation surrounding the wellbore. A first coil is wound around a cylindrical annulus core coaxial with the magnets, the core including high magnetic permeability material. The first coil produces pulsed RF magnetic fields oriented parallel to the axis of the apparatus and thus perpendicular to the static magnetic field in the toroidal examination region. This reorients certain nuclear spins and the bulk magnetization of the formation within the examination region resulting from them. The first coil picks up on component of the spin-echo signals of the precessing nucleii. A second coil toroidally wound around the same cylindrical annulus core in the form of a torus with windings in planes parallel to the axis of the apparatus detects a second component of the spin-echo signals. The apparatus also includes a third coil spaced apart from the first coil and having a geometry similar to that of the second coil. An electrically conducting collar shields the third coil from the magnetic fields produced elsewhere in the apparatus. A processor combines the signals from the three coils to give spin-echo signals with improved signal-to-noise ratio.

16 Claims, 3 Drawing Sheets

TOROIDAL RECEIVER FOR NMR MWD

BACKGROUND OF THE INVENTION

1. Field of the Invention

The present invention relates to the field of nuclear magnetic resonance (NMR) measurements and methods of measurement. Specifically, the present invention provides improved apparatus for sensing the NMR response of rock formations surrounding a wellbore deep in the earth using a device located in the wellbore although the improved sensing methods are not limited to use in a wellbore.

2. Background and Description of the Prior Art

A variety of techniques have are utilized in determining the presence and estimation of quantities of hydrocarbons (oil and gas) in earth formations. These methods are designed to determine formation parameters, including among other things, the resistivity, porosity and permeability of the rock formation surrounding the wellbore drilled for recovering the hydrocarbons. Typically, the tools designed to provide the desired information are used to log the wellbore. Much of the logging is done after the well bores have been drilled. More recently, wellbores have been logged while drilling of the wellbores, which is referred to as measurement-while-drilling ("MWD") or logging-while-drilling ("LWD").

One recently evolving technique involves utilizing Nuclear Magnetic Resonance (NMR) logging tools and methods for determining, among other things porosity, hydrocarbon saturation and permeability of the rock formations.

Stable nuclei have a quantized angular momentum Ih where the nuclear spin quantum number I is an integer multiple of ½ and Planck's constant h=2 πh. When I is not zero, the nucleus has an associated nuclear dipole magnetic moment $\mu = g\mu_h$ I where $\mu_h$ is the nuclear magneton defined below. This equation defines g, the nuclear gyromagnetic ratio, which is unique for each nuclear isotope. Since both protons and neutrons of which each nucleus is composed are fermions with spin ½, I is non-zero whenever the number of protons or the number of neutrons in the nucleus is odd.

It has long been known (i.e. since 1946) that the nuclear dipole magnetic moments of individual nuclei in a sample of matter align themselves with any externally applied steady state or static magnetic field, $H_0$, so that their projections along the axis of the field direction are quantized in one of 2I+1 states with magnitudes m=I, I−1, . . . −I. This produces a bulk magnetization along the direction of the applied magnetic field if the populations of the different magnetic substates differ as they normally do since the states are populated according to a Maxwell-Boltzmann distribution function. The magnitude of this bulk magnetization is thus proportional to the asymmetry in the populations of the magnetic substates with values of m equal in magnitude but opposite in sign and this asymmetry in turn is proportional to the energy difference between these substates which itself depends directly on the strength of the field $H_0$. Thus the bulk magnetization is proportional to $H_0$. The energy eigenvalues $E_m$ of these magnetic substates are given by the interaction of $\mu$ with the static field by the relation $$E_m = -\vec{\mu} \cdot \vec{H}_0 = -\frac{\mu}{I} \vec{I} \cdot \vec{H}_0 = -g\mu_h \vec{I} \cdot \vec{H}_0 = -mg\mu_h H_0 \qquad (1)$$

and transitions are allowed between neighboring states so that the nuclei may absorb or emit energy quanta with $E=h\nu=g\mu_h H_0$. Thus, if the different states are not equally populated, by irradiating the sample with an oscillating magnetic field of frequency $\nu=g$ $(\mu_h/h)H_0$, energy can be transferred to the system and this phenomenon is known as nuclear magnetic resonance or NMR for short since only at this frequency will energy be absorbed. The system behaves as a classical system in which the nuclear spins maintain fixed angles with the static field direction and precess about that direction with an angular frequency $\omega_0=2\pi\nu=g$ $(\mu_h/h)$ $H_0$ known as the Larmor precession frequency, where the nuclear magneton, $\mu_h$, is simply a scaling constant given by $\mu_h=(eh)/(2M_pc)=5.051\ 10$ joules per gauss, $M_p$ being the rest mass of the proton, e its charge and c the speed of light in a vacuum.

Since the resonance frequency is proportional to g, different nuclei precess about the static field direction at different frequencies. The nucleus with the largest g factor is the single proton which is the nucleus of the hydrogen atom for which g $(\mu_h/h)=26,752$ radians/gauss/sec and these nuclei precess at the highest Larmor frequency in the presence of any given static magnetic field. For strong static fields typically employed in NMR logging devices, protons precess at radio frequencies.

For example, with $H_0=0.1T=1,000$ gauss, $\nu=4.2577$ MHz.

When the radio frequency perturbing field is applied orthogonally to the static field, it exerts a coherent force on the nuclei selected with its frequency which is orthogonal to both the static field and perturbing field directions. If this perturbing field is applied for only a precisely appropriate time, the spins of the nuclei selected with this frequency will be rotated through an angle of 90° in the plane orthogonal to the direction of the radio frequency field. Such a finite length radio frequency (RF) perturbing field is called a $\pi/2$ or 90° pulse since it rotates the nuclear spins by exactly 90°. The field strength required for this 90° rotation may be very small compared to the static field strength since $\theta=\pi/2=g$ $(\mu_h/h)H_1 t_p$, where $H_1$ is the RF field strength, $\theta$ is the angle through which the nuclear spins are rotated by $H_1$ and $t_p$ is the length of time the RF field $H_1$ must be applied to rotate the bulk magnetization through the angle $\theta$. For protons, a mere 1 gauss $H_1$ will produce a $\pi/2$ rotation in only $t_p=58.7$ usec. When this 90° pulse ends, the nuclear spins gradually relax and return to their original alignment with the static magnetic field. The characteristic time for this process, $T_1$, which is called the longitudinal decay time in the art, is related to interactions between the nuclear spins of interest and the "lattice" in which they are held or the material in which they are imbedded and thus may be related to water saturation and rock permeability among other petrophysical parameters in the case of proton resonance in natural rock formations. This signal can in principal be detected by the same coil or antenna used to apply the perturbing 90° RF pulse: it would be the decay time of the strength of the RF signal observed at the Larmor frequency of the selected nuclei (i.e. hydrogen) as a function of time.

There are, however, difficulties in measuring $T_1$ directly by simple observation of the magnetization decay following such a pulse because other processes can contribute to the decay of the observed signal following a single 90° pulse which is known in the art as the free induction decay or FID signal. In particular, dipole-dipole interactions between the spins of neighboring nuclei may occur, significantly reducing the decay time. The characteristic time for relaxation by this process, $T_2$, is called the transverse decay time in the art and this too can be related to petrophysical quantities of interest such as producible or movable porosity, permeability to fluid flow, irreducible water saturation and fluid diffusion coefficients. In addition, local magnetic field inhomogeneities within the macroscopic sample examined whether caused by the geometry or asymmetry of the magnets producing the static field or by local magnetic property variations within the sample can produce a static distribution of precession frequencies for a given nuclear isotope also resulting in a much faster decay of the signal. The observed characteristic relaxation time of the FID signal is called $T_2^*$ and it results in line broadening of the observed RF signal from the sample roughly given by $\Delta f=(2\pi T_2^*)$ when the decay due to these phenomena is substantially faster than that due to spin-lattice interactions alone. This is the situation encountered in the detection of hydrogen in samples of sedimentary rock where the hydrogen nuclei are concentrated in the fluids contained in minute pores of the rock and where static field inhomogeneities in the sample volume can be substantial.

When $T_1 \gg T_2^*$ and the exciting 90° pulse is short with respect to $T_1$, the line broadening effects of static distributions in $\omega_L$ can be removed by employing a method known as the spin echo technique. As a result of inhomogeneities in the static field, those nuclei within the sample at locations with higher than average field strength precess faster and those at locations with lower than average field strength precess slower than those at locations with average field strength and a dephasing occurs destroying the signal coherence. However, this dephasing can be systematically repaired by application of a second RF magnetic field pulse of the same strength but twice the duration of the initial 90° pulse which is applied some time $\tau$ after the initial exciting pulse. Such a pulse for obvious reasons is called a $\pi$ or 180° pulse and it rotates the orientation of all the spins in the plane perpendicular to the RF field direction so that those nuclei which were advanced with respect to the average precessional position are now delayed and vice versa. Nevertheless, they are still situated at higher field strength locations and precessing faster than those at average field strength locations within the sample so that after a period of length $2\tau$ following application of the 180° pulse, the dephasing effects due to the inhomogeneous field produced in the time period between the 90° excitation pulse and the 180° pulse are reversed and a coherent spin echo signal may be detected. 180° RF pulses may be applied at successive intervals of $2\tau$ in a sequence first suggested by Carr and i)urcell, and modified by Meiboom and Gill to observe several spin echo signals which decay exponentially at a rate dependent on both $T_2$ and the square of the delay time $2\tau$ between successive RF pulses (see FIG. 2a). By varying $\tau, T_2$ can thus be determined from the amplitudes of the spin echo signals. $T_1$ can be determined either by direct measurement with a series of observations of the signal amplitude following application of a 180° pulse followed by a 90° pulse (a lengthy process) or by a series of 90° pulse sequences with different delay times between successive pulses in each sequence. In fact, a number of different pulsesequences may be employed to obtain information about the various microscopic physical processes which result in reorientation of the nuclear spins and both the theory of NMR, the spin echo method and a number of specific such pulse sequences are well discussed by Farrar and Becker. Instrumentation for switching and processing the RF NMR signals detected by the antenna coil is well-known in the art and is discussed in detail, for example in Clark.

Figure 2A:
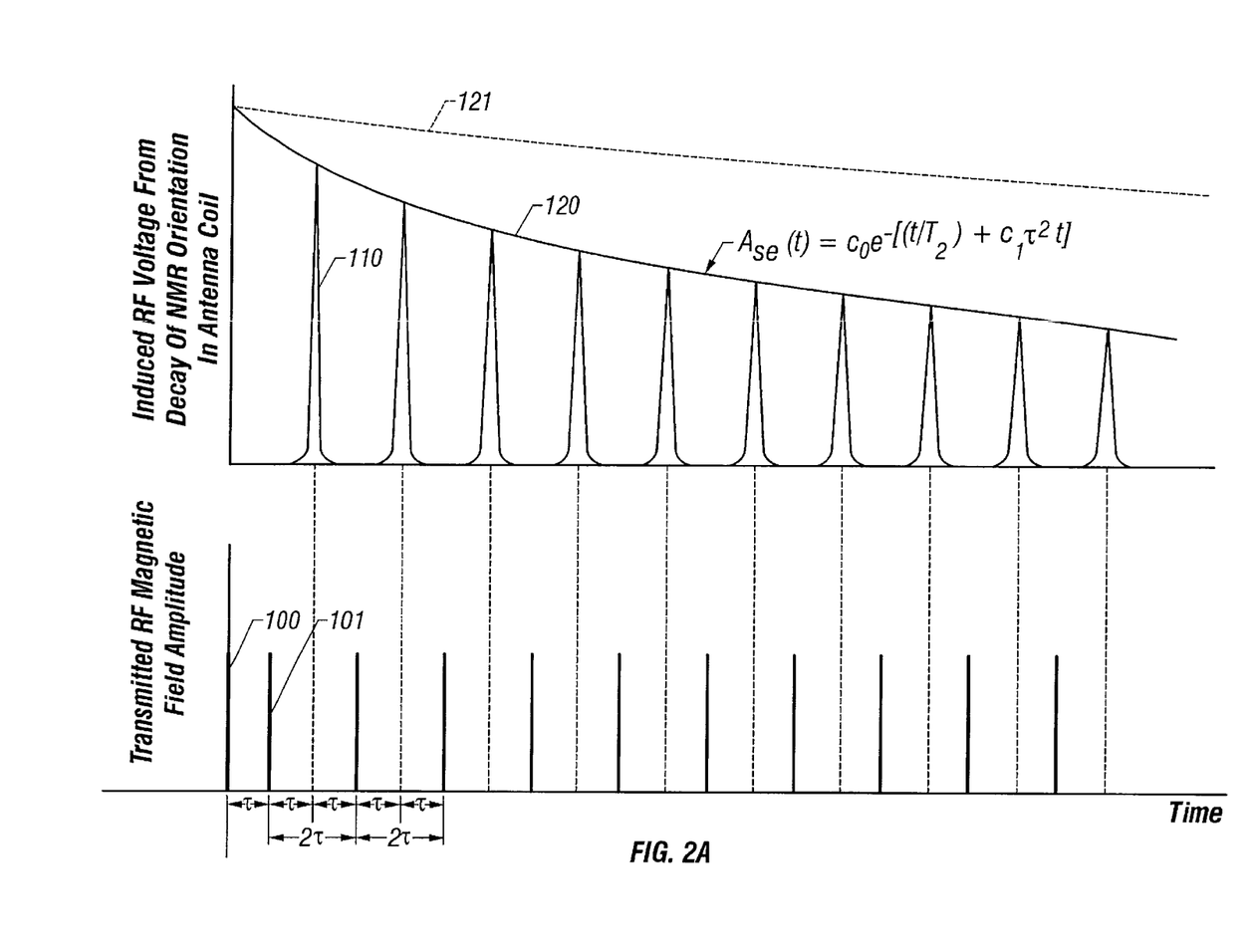
FIGS. 2a and 2b schematically illustrate the character of both transmitted and received RF signals in a pulsed NMR apparatus of the type illustrated in FIG. 1 and their sequence in time at two different time scales.
Figure 2B:
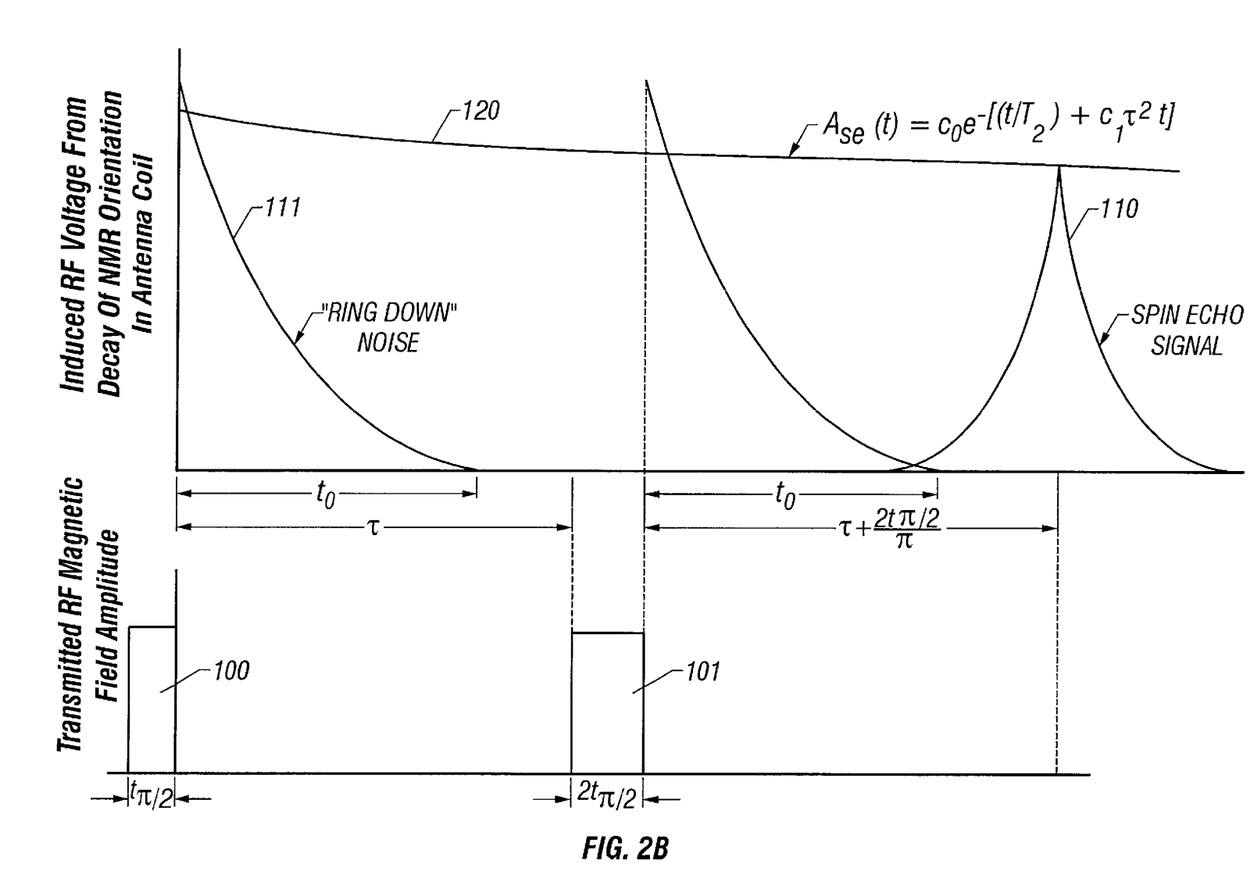

It is important to realize that since the same coil used to apply the RF magnetic field pulses is used to detect the NMR decay signals, there is a finite "dead time", $t_0$, following termination of each of the RF pulses during which the field collapses, energy in the transmitting coil circuit is damped out and the coil is switched to a detector circuit and thus can not be used as a detector (see FIG. 2b). The delay time $\tau$ between 180° RF pulses and the spin echo signals following them may be chosen sufficiently long with respect to $t_0$ so that the spin echo signals occur outside these dead time intervals, but the length of $t_0$ imposes a restriction on the possible delays, $2\tau$, between successive RF pulses which can be employed in the spin echo pulse sequence.

One NMR device employing this art for application in measuring some important characteristics of rocks in-situ using a device deployed in a borehole is described in U.S. Pat. No. 4,350,955 issued to Jackson et al. In this device two axially polarized cylindrical magnets are mechanically fixed in a coaxial arrangement with opposite polarities so that there is a gap between their like poles producing a toroidal region in the rock formation surrounding the axis of the tool in which there is a near-uniform radial magnetic field. These magnets may either be matched permanent magnets or electromagnets. A perturbing RF axial magnetic field is produced in this toroidal region by passing a RF alternating current through a coil whose windings lie substantially in planes perpendicular to the axis of the tool which is centered at the midpoint of the gap between the two magnets with which it is coaxial. After a period of time sufficient to rotate the bulk magnetization in the toroidal region by 90 in the plane perpendicular to the axis of the tool (i.e. the axis of the wellbore) from a radial to an azimuthal direction, the RF current is turned off and the coil is used as a detector to pick up the induced RF voltage resulting from the vertical component of the field induced by the coherently precessing hydrogen nuclei in the toroidal region and thus to measure the decay time as the bulk magnetization decays to its radial alignment in which the net vertical component of the magnetization resulting from the precessing protons is zero. This device has the advantage of providing a homogeneous static field only in a large region within the rock formation far from the wellbore and thus largely avoiding a spurious signal from fluids in the wellbore such as drilling mud which would not provide information about the undisturbed rocks or the fluids contained in their pores. In addition the substantial static magnetic field used to align the hydrogen nuclear spins in the sample region radially with respect to the wellbore axis provides for a substantial improvement in the signal-to-noise ratio of the RF NMR signal over devices which rely on the weak magnetic field of the earth to provide the initial polarized magnetization. Signal-to-noise ratio can be further enhanced by the inclusion of a high magnetic permeability ferrite in the interior of the antenna coil as described in U.S. Pat. No. 4,629,986 issued to Clow et al.

Three difficulties with devices of this type have been described in U.S. Pat. No. 5,712,566 issued to Taicher and Reiderman. First, they point out that the geometry of the static aligning field is severely limited in the axial direction so that the device may move substantially with respect to the region in which the precessing nuclei have been properly oriented prior to the RF pulse sequence during the normal course of wireline logging since the tool is normally moved at a rate of at least 10 feet per minute and observations may require as long as several seconds to obtain measurements of the characteristic decay times $T_1$ and $T_2$. Miller et al. (1990), however, claim useful independent measurements made at 0.2 foot intervals and pulse sequences requiring no more than several tenths of a second.

Second, Taicher and Rederman disclose that the geometry provided by the device described in '955 does not eliminate NMR signal from the fluid filling the wellbore adjacent to the tool. As elucidated in U.S. Pat. No. 4,717,876 issued to Masi and Miller, this results from the details of the shape of the field produced by the arrangement of magnets described in '955 above and below the mid-plane between the two magnets which produce the static field and perpendicular to their axis. In this region, "skirts" of high magnetic field intensity exist much closer to the axis of the magnets within the logging tool than in the toroidal examination region centered in the mid-plane between the magnets and in this region proximal to the logging tool, borehole fluids are found.

Finally, they point out that spatial variations in the magnetic field of the earth or in the temperature of the magnets in the logging tool as the tool is moved in the borehole can affect the static field strength in the toroidal sample region and thus the NMR signal frequency so that the observed signal at a fixed frequency may not originate in the toroidal region described and that no method is provided in '955 to compensate the RF frequency for such changes in the static field strength. This too seems at most to be a minor difficulty since the magnetic field of the earth is almost everywhere less than 0.5 gauss which is very small compared with the static radial field strengths of at least 100 gauss produced by the magnets in the tool within the toroidal sample region shown in FIG. 5 of the '955 patent.

An additional drawback of the Jackson and Cooper '955 device is the spurious signal in the antenna produced by magnetoacoustic coupling. The RF current induced within the skin depth of a conductor located in a static magnetic field when it is irradiated by a RF magnetic field interacts with the lattice of the conductor through the Lorentz force to produce an ultrasonic acoustic wave of the same radio frequency which radiates into the conductor setting up a standing wave. By the reciprocal mechanism, the acoustic waves propagating in a conductor located in a static magnetic field produce an oscillating magnetic field of the same frequency. In an NMR apparatus such as many of those employed in borehole logging devices there are frequently several conducting components located within the static magnetic field and the pulsed RF magnetic field in which this phenomenon can occur. They may include the tool mandrel or the drill pipe, any conductor with high magnetic permeability such as ferrite used to intensify the induced field within the RF detection coil and the metal wires of the RF coil/antenna themselves. During the time the RF magnetic field pulse is applied, RF ultrasonic acoustic standing waves are set up in these conductive components. When the RF field is switched off, however, the RF magnetic fields produced by these acoustic waves are detected by the RF antenna and these signals decay only at the rate governed by loss of energy of the acoustic wave in the conductor which is very much slower than the typical decay rate of an FID signal. The period during which such signals predominate over that resulting from decay of the nuclear spin orientations within the examination region in the rock formation may thus be long with respect to the dead time due to damping in the electrical circuit containing the detection antenna or the collapse of the magnetic field itself or even with respect to the interval, $\tau$, between cessation of the RF magnetic field pulse and occurrence of the spin echo signal from it. This slow decay of a strong induced magnetoacoustic signal is known in the art as coil "disease" or "ring down" (see FIG. 2b). This phenomenon can restrict the delay times between pulses which can be used and hence, the number of spin echoes which can be observed in a given time which in turn can affect the precision and even the accuracy of $T_2$.

Still another drawback of the '955 device is the possibility of "magnetostrictive ringing" resulting from the cessation of the RF magnetic field at the end of an individual pulse. When this magnetic field changes, the bulk magnetization of the material affected by the field is altered and this results in a change in the size of the material producing an elastic disturbance. Since the disturbance is excited by a pulse of a given frequency it has a long duration. This phenomenon, known as magnetostriction, also can result in an oscillatory signal of significant duration at the Larmor precession frequency not related to the decay of the nuclear spin alignment which can mask the signal of interest and so lengthen the dead time within which the NMR signal can not be observed with sufficient signal-to-noise ratio to be of use.

A final difficulty of the device described in '955 is the relatively weak signal strength which can be achieved with it. The NMR signal strength depends primarily on the size of the examination region, the strength of the static magnetic field and its homogeneity in that region. While the examination region is reasonably large and the homogeneity of the field is excellent in both the azimuthal and radial directions at least, the relatively weak peak field strength in the examination region of only approximately 100 gauss leads to a rather weak NMR signal.

An improvement in devices of this type is disclosed in U.S. Pat. No. 4,717,876 issued to Masi and Miller. This invention discloses the addition of radial polarized ring magnets in the form of a cylindrical annulus coaxial with the two primary longitudinal magnets producing the static field described in '955 and located in the gap between them. These ring magnets serve several purposes. These radially polarized magnets boost the magnitude of the radial static field at all radial distances near the midplane between the two primary magnets and in particular in the toroidal examination region. In addition, they create a more homogeneous field within the toroidal examination region and increase its diameter, thus providing a greater volume of rock deeper in the formation from which the NMR signal can be observed which improves both signal-to-noise ratio and also measurement accuracy. Still further, the addition of these magnets significantly increases the radial field strength near the wall of the logging tool above and below the midplane between the two primary magnets eliminating the "skirt" regions of homogeneous field from which spurious signals originating in the wellbore fluids may be detected. Finally, Masi & Miller disclose constructing these additional magnets from electrically non-conductive materials in order to suppress magnetoacoustic and magnetostrictive ringing in these components. They claim to produce a homogeneous radial field strength of 360 gauss at distances 5 to 7 inches from the axis of the logging tool as compared with field strengths of approximately 270 gauss at radial distances of 4.0 to 5.8 inches from the axis of the tool using similar types of primary magnets in the arrangement described in '955 but without the additional ring magnets.

A difficulty with the apparatus disclosed in '876 is that the RF transmitter/receiver antenna is located in a region of much higher static field strength than in the apparatus disclosed in '955 and is therefore much more vulnerable to coil "disease".

A second drawback to the apparatus disclosed in '876 is that the static field strength nearer the logging tool axis than the toroidal examination region is higher than that in the examination region itself unlike the field produced by the apparatus disclosed in '955. This means that nuclei in parts of this region with lower gyromagnetic ratios than hydrogen may precess at precisely the same Larmor frequencies and produce a NMR signal masquerading as hydrogen from the examination region.

Another type of NMR well logging apparatus is is described in U.S. Pat. No. 4,710,713 issued to Strikman and in U.S. Pat. No. 5,212,447 issued to Paltiel. In these devices, the static magnetic field is provided by a permanent cylindrical magnet composed of a non-conductive material coaxial with the longitudinal axis of the logging tool and substantially with the wellbore axis which is polarized in a direction perpendicular to this axis. The RF magnetic fields are provided in a direction perpendicular to both the tool axis and the polarization of the cylindrical magnet by circulating a current through a coil surrounding the magnet with windings substantially lying in planes parallel to both the polarization of the static magnetic field and the axis of the tool. This apparatus provides a substantially uniform static magnetic field of a given strength and an orthogonal RF magnetic field within much of a thin cylindrical annulus of the rock formation surrounding the borehole. NMR signals excited in this region are received by the coil which may be tuned to a range of RF frequencies to investigate regions of varying radius from the longitudinal axis of the apparatus.

A number of difficulties with this type of device have been identified in U.S. Pat. No. 5,712,566 issued to Taicher and Reiderman. Even though the magnets are composed of non-conductive material and thus do not contribute to magnetoacoustic or magnetostrictive ringing, significant magnetoacoustic and magnetostrictive ringing still does occur from the waves induced in the conductive coil windings themselves which are located in a region of high static field strength. In addition, an electrically conductive fluid in the wellbore which commonly includes formation waters or drilling mud that can be quite saline and, therefore, conductive can effectively shield most of the RF energy from the region of examination in the rock formation so that only the fluids in the borehole contribute significantly to the NMR signal observed. Further problems include the lack of resolution resulting from the required length of the coil which must be substantially greater than the diameter of the annular region of examination. Even when this condition is met, the static field strength decreases as the square of the radial distance from the axis of the magnet providing only a thin region in which this field is nearly homogeneous and has a near-constant gradient.

Further difficulties with devices of this type include an inherently weaker static magnetic field which can be achieved with non-conductive magnets which results in lower signal strength and consequently potentially lower signal-to-noise ratio than can be obtained with prior art devices and also the reduction in the strength of the NMR signal which results from the necessary absence of high magnetic permeability conductive cores or yokes in connection with the RF antenna as disclosed by Clow et al. in '986.

Yet another potential difficulty with devices of this type lies in the nature of the static magnetic field employed which decreases monotonically as the square of the distance from the axis of the magnets. Such a field allows nuclei with lower gyromagnetic ratios than hydrogen located in a region nearer the wellbore than the examination region to precess at the same Larmor precession frequency and thus contribute a spurious coherent signal masquerading as hydrogen from the examination region.

Yet another device is described in U.S. Pat. No. 5,712,566 issued to Taicher and Reiderman which attempts to rectify some of these difficulties. In it the static magnetic field is provided by a long non-conductive permanent magnet in the form of a circular or elliptical annulus coaxial with the logging tool which is again linearly polarized in one direction perpendicular to its axis. This provides a cylindrical or elliptical interior region in which no substantial static magnetic field exists and in which an RF transmitting/receiving antenna coil is provided coaxial with the magnet to reorient the nuclear spins and also observe the decay of the NMR signals from a thin cylindrical or elliptical annular examination region in the rock formation. A high magnetic permeability cylindrical ferrite core is provided inside the RF antenna coil to increase its efficiency and still another coil is wound around that core to provide a weak static axial magnetic field so as to permit the magnetic permeability of the core to be varied and thus allow the tuning frequency of the antenna to be varied. An additional sensing coil is also included outside the permanent magnet with windings substantially in planes parallel to that containing both the axis of the permanent magnet and its direction of magnetization. This coil is thus insensitive to the RF field produced by the antenna coil which is parallel to it and so can detect NMR signals from the region of examination in the rock formation at very short times after the end of an RF pulse. Since the RF antenna coil is not located in a region of high static magnetic field strength, coil "disease" is substantially attenuated in this sensor though presumably not in the additional sensing coil which is located, at least in part, in a region of high static magnetic field strength. In addition, this coil may be made short with respect to the length of the permanent magnet unlike the RF antenna described above in '713 and '447, thus improving the vertical resolution of the measurement. This device, however, still suffers from the lower static field strengths produced by the necessarily non-conducting magnets and from the nature of the radial dependence of the static magnetic field strength.

A significant feature of merit of any NMR logging device is the signal-to-noise ratio (SNR) of the measured RF voltages resulting from the decay of the nuclear spin orientations. This SNR determines both the precision with which the spin echo amplitudes can be measured as well as the length of the pulse sequence which can be observed and thus the accuracy with which the decay times $T_1$ and $T_2$ can be measured. Devices with high SNR values are preferable.

A second feature of merit is the dead time required following cessation of any particular RF pulse before an observation of the RF field from nuclear spin orientation decay can be made (i.e. $t_0$ in FIG. 2b). Devices with short dead times are preferable as they allow many more spin echo observations to be made in a given amount of time thus increasing the efficiency of the device and also permit a wider range of delay times between pulses (i.e. $2\tau$ in FIG. 2b) to be employed.

It is an object of the present invention to provide a NMR measurement apparatus suitable for use in a wellbore with higher signal-to-noise ratio than those known from prior art. It is another object of the present invention to reduce the strength of the magnetostrictive and magnetoacoustic "ring down" signals not only to improve the signal-to-noise ratio of the NMR detection apparatus but also to shorten the dead time following cessation of RF pulses within which no observation of the NMR signal from the rock formation may be made and thus allowing for a wider range of choices for the delay time, $2\tau$, between RF pulses.

SUMMARY OF THE INVENTION

The present invention is a nuclear magnetic sensing apparatus suitable for use in a substantially cylindrical borehole either in wireline or measurement-while-drilling applications. It employs either electromagnets or permanent magnets oppositely polarized in the axial direction and suitably arranged along the axis of the apparatus to produce a nearly radial static magnetic field in a toroidal examination region within the rock formation surrounding the wellbore distant from the axis of the apparatus. A first coil is wound around a cylindrical annulus core coaxial with the magnets, the core including high magnetic permeability material. The first coil has with in planes substantially perpendicular to the axis of the apparatus to produce pulsed RF magnetic fields oriented parallel to the axis of the apparatus and thus perpendicular to the static magnetic field in the toroidal examination region. This reorients certain nuclear spins and the bulk magnetization of the formation within the examination region resulting from them. The device includes a second coil toroidally wound around the same cylindrical annulus core in the form of a torus with windings in planes composed substantially of only axial and radial components with respect to the axis of the apparatus. The second coil detects particular components of the magnetic fields induced by the aligned nuclear spins in the examination region during the intervals between the application of the RF magnetic field pulses. The apparatus also includes a third coil wound around a second high magnetic permeability cylindrical annulus also coaxial with the apparatus described above. This third coil is axially separated from the magnets which produce the static magnetic field and also from the other coils which produce and/or detect RF magnetic fields by an electrically conducting collar. The third coil is, like the second coil, toroidally wound. The electrically conducting collar shields the third coil from the magnetic fields produced elsewhere in the apparatus. The third coil measures the azimuthal magnetic field with respect to the axis of the apparatus resulting from the induced current in the electrically conductive logging tool mandrel or drill pipe resulting from the tangential component of the RF magnetic field produced by bulk magnetization in the examination region

BRIEF DESCRIPTION OF THE DRAWINGS

For detailed understanding of the present invention, reference is made to the following detailed description of the preferred embodiment taken together with the accompanying drawings in which like elements have been given like numerals.

DETAILED DESCRIPTION OF THE PREFERRED EMBODIMENTS

In general, the present invention provides an improved method of detecting a weak signal from the rock formation by reducing sensitivity to the principal causes of noise and increasing the strength of the desired signal in NMR devices with static magnetic field and RF transmitter/receiver coil geometry of the type disclosed by Jackson and Cooper in U.S. Pat. No. 4,350,955.

Figure 1:
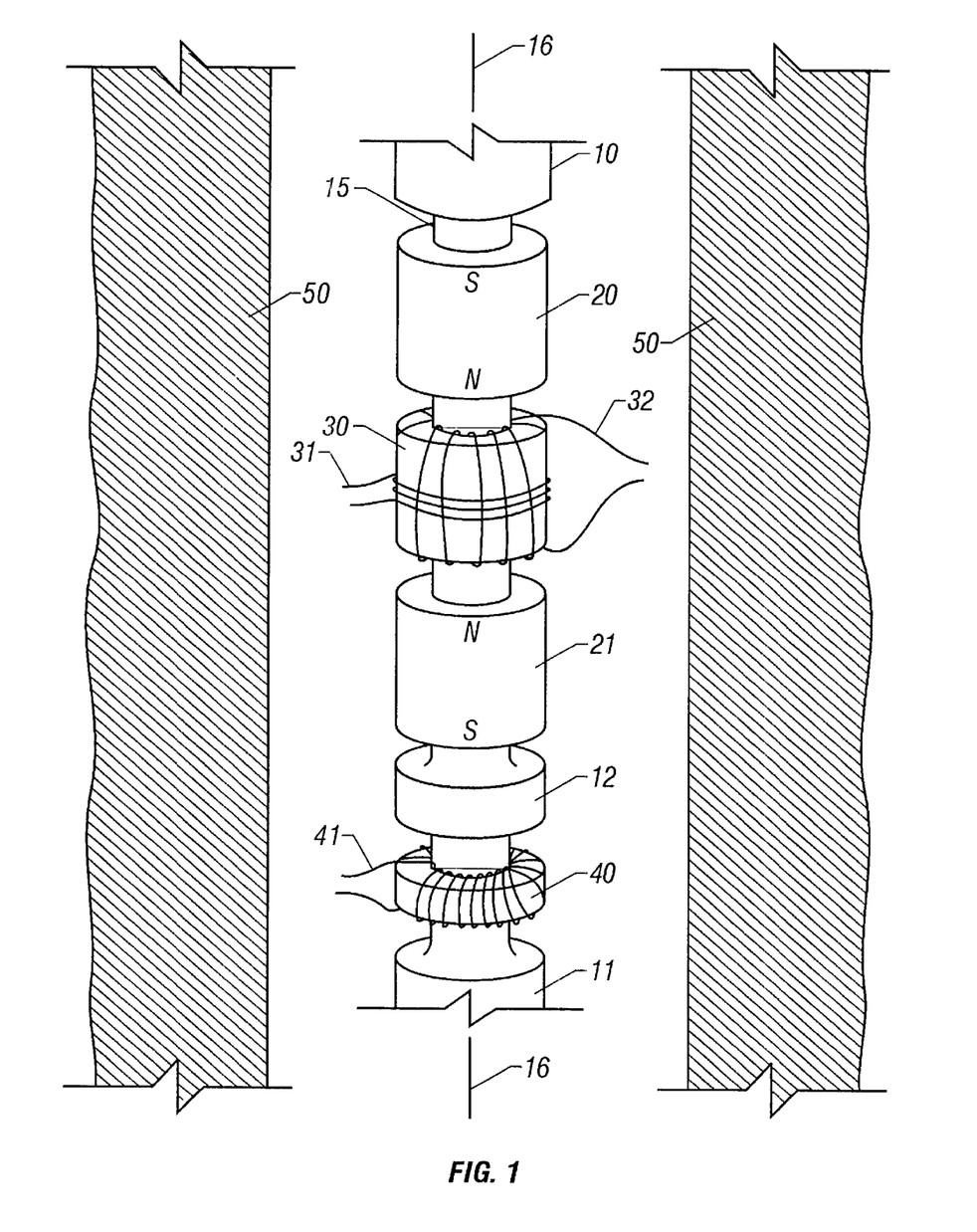
FIG. 1 shows a NMR excitation and detection apparatus including preferred embodiments of the present invention suitable for deployment in a wellbore and for detection of NMR signals from rock formations surrounding the wellbore.

FIG. 1 shows a schematic diagram of a borehole tool of the type disclosed in '955 with the improvements of the current invention. Metal subassemblies 10 and 11 provide a means of coupling the apparatus to the drill string for measurement while drilling or to a wireline or other wireline logging devices. The entire assembly is enclosed within a suitable casing (not shown) for wireline applications while for MWD applications, the assembly is enclosed within a drill collar (not shown) provided with a hollow axial cavity for passage of drilling mud.

Two permanent cylindrical magnets 20 and 21 with opposite longitudinal polarizations are mounted on the tool mandrel 15 with their longitudinal axes aligned with that of the entire apparatus 16 which is substantially aligned in coincidence with the axis of the wellbore with a gap between their like poles providing a nearly uniform static radial magnetic field in a toroidal region of the rock formation 50 surrounding the borehole between the two permanent magnets. A cylindrical annulus core 30 composed of high magnetic permeability material such as soft ferrite and coaxial with the two permanent magnets is mounted on the tool mandrel equidistant between the two permanent magnets. A first coil 31, designated herein as coil A, transverse to the longitudinal axis of the apparatus is wrapped around core 30 with windings lying in planes substantially perpendicular to this axis. This coil is used both as a transmitter for providing the RF magnetic field in the region of examination and as a receiver for sensing the decaying axial component of the RF NMR echo signal when the applied RF field is terminated.

A second coil 32, designated herein as coil B, is wrapped around core 30 in the form of a torus to allow sensing of the azimuthal or tangential component of the RF field produced by the precessing nuclear spins in the rock formation during decay of its magnetization orientation. As the bulk magnetization orientation in the rock formation returns to a radial direction following the application of pulses of the RF magnetic field, the axial component of the RF magnetic field produced by the precessing proton spins decreases resulting in a decreasing signal in coil A but at the same time the azimuthal component of this field increases producing an increasing signal in coil B, i.e., the two signals have a $\pi/2$ phase shift relative to each other.

Using known signal processing techniques and based upon an estimate of the signal-to-noise ratio of the signals on the two coils, an improved estimate of the spinecho envelope is obtained by applying a $\pi/2$ to the signal from one coil and combining it with the signal from the other coil using a scaling factor dependent upon the signal-to-noise ratio.

A third coil, 41, designated herein as coil C, is wound in the form of a torus around another cylindrical annulus core, 40, also composed of high magnetic permeability material such as soft ferrite which is also mounted coaxial with the longitudinal axis of the apparatus and spatially separated from the magnets and coils of the rest of the apparatus by an electrically conducting collar 12 which shields coil C from the magnetic fields produced by magnets 20 and 21 as well as those produced by currents circulating in coils A and B. The azimuthal component of the RF magnetic field produced by precessing protons in the rock formation induces a longitudinal RF electrical current in the electrically conductive body of the apparatus which in turn induces an RF azimuthal magnetic field around the body of the apparatus which can be detected by coil C. This coil which is not located in a region of high intensity static Magnetic field does not suffer from the coil "disease" described above and common in previous devices so it allows NMR signals to be observed at much shorter times following cessation of the RF magnetic field pulses than is possible with devices utilizing the prior art and hence, allows shorter delay times between RF magnetic field pulses to be employed which permits more spin echo observations to be made in a given amount of time increasing the efficiency and/or resolution of the measurement.

Turning now to FIG. 2a, the lower portion shows an example of the applied RF pulse sequence. In this example, the pulse sequence comprises an initial π/2 tipping pulse 100 followed by a sequence of equally spaced the refocusing pulses 101 separated by intervals of duration 2τ beginning at a time τ following the end of the tipping pulse. Typically, the refocusing pulses have a pulse duration sufficient to reorient the pulse by π. The tipping pulses and the refocusing pulses are applied to the coil 31. Following the cessation of each of these applied RF pulses, coil 31 is rapidly switched to become a receiver coil. At a time of approximately τ following cessation of each π pulse, a spin echo signal 110 is observed in coil 31 as well as in coils 32 and 40. The polarity of the successive spin echo signals has been reversed in FIG. 2a for simplicity of depiction. The peak amplitude of the spin echo signals decays exponentially as a function of time following application of the tipping pulse as indicated by envelope 120 that is dependent upon the transverse relaxation time $T_2$ and the square of the delay time 2τ by a relation of the form:

$$A_{se}(t) = C_0 e^{-[(\frac{t}{T_2}) + C_1 \tau^2 t]}$$

where A se (t) is the peak amplitude of the spin echo signal 110 at a time t following cessation of the initial tipping pulse 100 and $C_0$ and $C_1$ are constants depending upon the geometry of the apparatus and the material properties of the sample being examined.

Alternatively, a sequence of π/2 pulses uniformly separated in time by intervals of length τ may be used to obtain a value of the longitudinal relaxation time $T_1$ as indicated by the dashed curve 121. In this case, the amplitude of the spin-echo signal obtained after a sufficiently long period following application of the initial tipping pulse is dependent upon both τ and $T_1$ so that measurement of these amplitudes for two or more values of τ may be used to determine $T_1$.

Turning now to FIG. 2b, the same signals are depicted on an expanded time scale from the application of the initial tipping pulse 100 to the end of the first spin echo signal. Immediately after the cessation of the pulse 110 that is π/2 pulse, the signal 111 observed on coil 31 may be quite large and consists primarily of various noise components, the longest of which are frequency due to magnetoacoustic or magnetostrictive ringing within the NMR apparatus. These noise signals have large amplitudes relative to the spin echo signal 110. The amplitude of this "ring down" noise dies out with time due to physical processes in the apparatus and after a time to following the cessation of each applied RF pulse, the noise is sufficiently small that the weak spinecho signals of interest may be observed. In FIGS. 2a and 2b, for simplifying the illustration, thermal noise is not shown: in reality, this thermal noise may also be quite large.

Following the initial tipping pulse 100, due to inhomogeneities in the sample and the magnetic field, the NMR signals start to dephase an a refocusing pulse 101 is applied to systematically remove these dephasing effects and to generate a spin-echo signal 110. It is a common practice in the art for this refocusing pulse to consist of a signal having the same amplitude but twice the duration of the tipping pulse, as depicted in FIG. 2b. "Ring down" occurs following the refocusing pulse as well. The NMR spin-echo signal of interest 110 is formed when the dephasing effects are exactly removed. When the tipping pulse is a π/2 pulse and the refocusing pulse is a π pulse, this occures at a time τ+(2/π) $t_{\pi/2}$. The peak amplitude, is $$A_{se}\left(t = 2\tau + 2\left(1 + \frac{1}{\pi}\right)t_{\pi/2}\right) = C_0 e^{-\left[\frac{2\{\tau + (1+\frac{1}{\pi})t_{\pi/2}\}}{T_2} + C_1 \tau^2 \{\tau + (1+\frac{1}{\pi})t_{\pi/2}\}\right]}$$

in conformity with the decay envelope 120 as described above. The time of the tipping pulse $t_{\pi/2}$ is directly proportional to the RF field strength, and even for very weak free induction decay (FID) signals, is characterized by a time constant $T_2^*$ that is, in borehole logging devices, much smaller than $T_1$ or $T_2$.

Those versed in the art would recognize that the method of the invention, i.e., recording two components of the precessing nuclear spins may be also used with other arrangements of the permanent magnets and RF coils than the apparatus described above. Specifically, when the static field is produced by a cylindrical magnet in which the magnetization axis is perpendicular to the longitudinal axis of the tool, a pair of cross-dipole RF coils may be used to record the two components of the precessing signal. Such variations are intended to be within the scope of the present invention.

It should be understood that the invention is in no way limited to the described embodiments, and that many changes may be made to these embodiments without departing from the scope of the present invention. Other embodiments would be obvious to those versed in the arts to which the invention pertains.

We claim:

1. An apparatus for determinating a parameter of interest of a subsurface formation in the vicinity of a borehole comprising:

(a) a magnet arrangement on a downhole tool for producing a static magnetic field having a substantially uniform field strength in a region of examination in the formation and aligning nuclear spins in said region parallel to a direction of said static magnetic field in said region;

(b) a first coil on the downhole tool for transmitting a pulsed radio frequency (RF) magnetic field into said region of examination, said first coil having windings around a first toroidal core having an axis parallel to said axis of the borehole, said first coil windings lying in a plane perpendicular to said axis of the borehole said first toroidal core intensifying the magnetic flux in the first coil, said pulsed RF field substantially perpendicular to said static field and inducing precession of nuclear spins in said region of examination, said first coil further receiving a first component of echo signals from said precessing nuclear spins and producing a first signal;

(c) at least one other coil on the downhole tool for receiving a second component of echo signals from the precessing nuclear spins and producing at least one second signal, said second component orthogonal to the first component, and (d) a processor for combining the first signal and the at least one second signal to determine the parameter of interest.

2. The apparatus of claim 1 wherein said magnet arrangement further comprises a pair of magnets having a magnetization direction parallel to an axis of the borehole, said pair of magnets disposed with like poles facing each other, said static field having a radial direction in the region of examination.

3. The apparatus of claim 2 wherein the first coil comprises windings in a plane orthogonal to said axis of the borehole.

4. The apparatus of claim 1 wherein the at least one other coil comprises a second coil having windings about the first toroidal core, said windings lying in planes parallel to said axis of the borehole.

5. The apparatus of claim 1 wherein the first toroidal core comprises a high magnetic permeability material.

6. The apparatus of claim 5 wherein the high permeability magnetic material comprises a ferrite.

7. The apparatus of claim 4 wherein the at least one other coil comprises a third coil spaced apart from the first coil, said third coil comprising windings around a second toroidal core spaced apart from the first coil and said windings lying in planes parallel to said borehole axis, said spaced apart second toroidal core separated from the first coil by an electrically conducting segment of the downhole tool wherein said electrically conducting segment shields the second coil from the magnet arrangement and currents in the first coil and the second coil.

8. The apparatus of claim 7 wherein the spaced apart second toroidal core comprises a high magnetic permeability material.

9. The apparatus of claim 8 wherein the high permeability magnetic material comprises a ferrite.

10. The apparatus of claim 1 wherein the processor is at a location selected from (i) on the downhole tool, and, (ii) at a surface location.

11. The apparatus of claim 1 wherein the downhole tool is conveyed on one of (i) a drillstring, (ii) a wireline, and, (iii) a coiled tubing.

12. The apparatus of claim 1 wherein the processor applies a phase shift to the at least one second signal relative to the first signal.

13. A method of determinating a parameter of interest of a subsurface formation in the vicinity of a borehole comprising:

(a) conveying a downhole tool into the borehole, the downhole tool having a magnet arrangement for producing a static magnetic field having a substantially uniform field strength in a region of examination in the formation and aligning nuclear spins in said region parallel to a direction of said static magnetic field in said region;

(b) using a first coil on the downhole tool for transmitting a pulsed radio frequency (RF) magnetic field into said region of examination, said pulsed RF field substantially perpendicular to said static field and inducing precession of nuclear spins in said region of examination, said first coil having windings around a toroidal core, said core having an axis parallel to said axis of the borehole, said windings in a plane perpendicular to said axis of the borehole;

(c) receiving in said first coil a first component of echo signals from said precessing nuclear spins and producing a first signal;

(d) receiving in a second coil proximate to the first coil on the downhole tool a second component of echo signals from the precessing nuclear spins and producing a second signal, said second component orthogonal to the first component, and (e) using a processor for combining the first signal and the second signal to determine the parameter of interest.

14. The method of claim 13 wherein combining the first signal and the second signal further comprises applying a phase shift to the second signal relative to the first signal.

15. The method of claim 14 wherein combining the first signal and the second signal further comprises weighting the first and second signals and summing the weighted first and second signals.

16. The method of claim 13 further comprising:

(i) receiving in a third coil spaced apart from the first coil the second component of the echo signals from the precessing nuclear spins to give a third signal; and (ii) using the processor to combine the third signal with the combination of the first and second signals.

* * * * *